US00PP35736P2

(12) United States Plant Patent
Hansen

(10) Patent No.: US PP35,736 P2
(45) Date of Patent: Apr. 9, 2024

(54) ***HIBISCUS* PLANT NAMED 'COOKIES AND CREAM'**

(50) Latin Name: ***Hibiscus* hybrid (L.)**
Varietal Denomination: Cookies and Cream

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 18/445,449

(22) Filed: Aug. 22, 2023

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt

(57) ABSTRACT

A new and distinct cultivar of winter-hardy, herbaceous, perennial, hybrid *Hibiscus* plant named 'Cookies and Cream' comprising a rounded mound habit of multiple, well-branched, basal stems producing flowers beginning in late July to early August and continuing for at least ten weeks, with the distal unbranched portion of peduncle producing multiple flowers in succession at a single node. Slightly cupped flowers have highly overlapping petals of white with a white eye. The foliage is primarily three-lobed with strong chocolate coloration. The new plant is useful in the landscape as a specimen or in mass.

2 Drawing Sheets

Botanical classification: *Hibiscus* hybrid (L.).
Variety denomination: 'Cookies and Cream'.

STATEMENT REGARDING PRIOR DISCLOSURES UNDER 37 CFR 1.77(B)(6)

The first offer for sales was by Walters Gardens, Inc on Dec. 14, 2022. Walters Gardens, Inc. obtained the new plant and all information relating thereto, from the inventor. No plants of *Hibiscus* 'Cookies and Cream' have been sold, in this country or anywhere in the world, by any name, nor has any disclosure of the new plant been made more than one year prior to the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Cookies and Cream' hybridized under the direction of the inventor on Aug. 18, 2020, at a wholesale perennial nursery in Zeeland, Michigan. The new plant is a self-pollination of the unreleased, proprietary hybrid known as 19-268-1 (not patented). During the trial process, the new plant was assigned the breeder code labeled 20-275-3. The parent has a complex mixture of species in them, believed to be comprising the species: *moscheutos, lasiocarpos, grandiflora*, and *coccineus*.

*Hibiscus* 'Cookies and Cream' was first asexually propagated in the late summer of 2021 by sterile shoot-tip tissue culture and later by shoot-tip cuttings at the same nursery in Zeeland, MI. The resultant asexually propagated plants have found both propagation methods to be stable and true to type in successive generations of asexual reproduction.

BRIEF SUMMARY OF THE PLANT

*Hibiscus* 'Cookies and Cream' differs from its parents as well as all other hardy herbaceous *Hibiscus* known to the applicant in many traits. The most similar *Hibiscus* known to the applicant are: 'Blue River II' (not patented), 'French Vanilla' U.S. Plant Pat. No. 33,181, 'Angel Eyes' U.S. Plant Pat. No. 35,455 and 'Marshmallow Moon' U.S. Plant Patent co-pending application Ser. No. 18/445,450.

'Blue River II' has a taller and more open upright habit with the flowers in the upper part of the plant, and the flowers are flatter with narrower and less imbricate petals. 'French Vanilla' has a slightly larger habit, the foliage is olive-green and less burgundy-tinted, the flowers open creamy-yellow and become creamy-white with intense sun and high temperatures, and have a reddish center and begins flowering later in the season. 'Angel Eyes' has a much larger habit, dark green foliage, and the flowers are near-white with a shiny deep-red eye and raspberry-red veins. 'Marshmallow Moon' has a slightly taller habit. All of the above cultivars produce single flowers per node and have green foliage compared with the multiple flowers in succession per node and chocolate-colored foliage of 'Cookies and Cream'.

The parent has a more open habit with more dissected foliage, and less burgundy coloration, the flowers are smaller and held tighter inside the foliage with fewer flowers per stem and per plant.

*Hibiscus* 'Cookies and Cream' is a unique hardy herbaceous *Hibiscus* with the following combined traits:

1. Winter-hardy, densely-compact perennial with a rounded mounded habit of multiple, well-branched, basal stems;
2. Rotate flowers with highly overlapping petals of white without a reddish eye;
3. Flowering beginning in late July to early August and continuing for at least ten weeks;
4. Distal unbranched portion of peduncle producing multiple flowers in succession at a single node;

5. Corolla slightly cupped with the leading inside edge of petals frequently folded underneath producing greater strength to withstand wind and rain;
6. Three-lobed foliage with strong chocolate coloration.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, temperature, and direction may cause the appearance of minor variations in color.

DETAILED BOTANICAL DESCRIPTION

Figure 1:
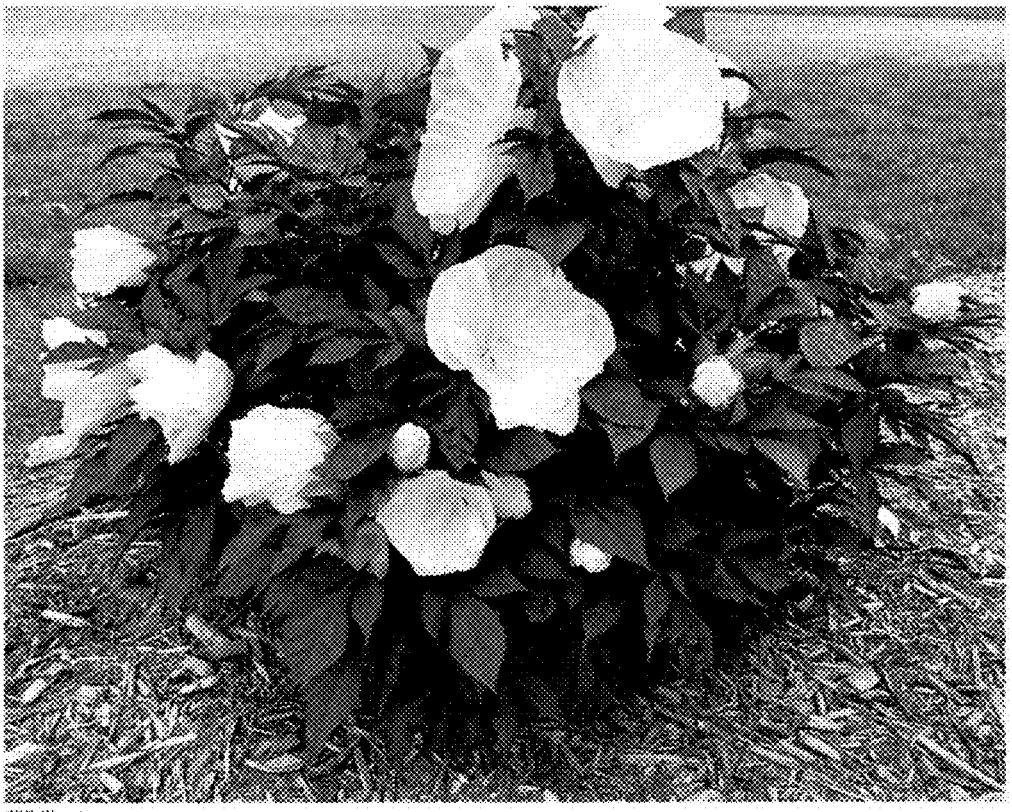
FIG. 1 shows a four-year-old plant in full flower in a display garden.
Figure 2:
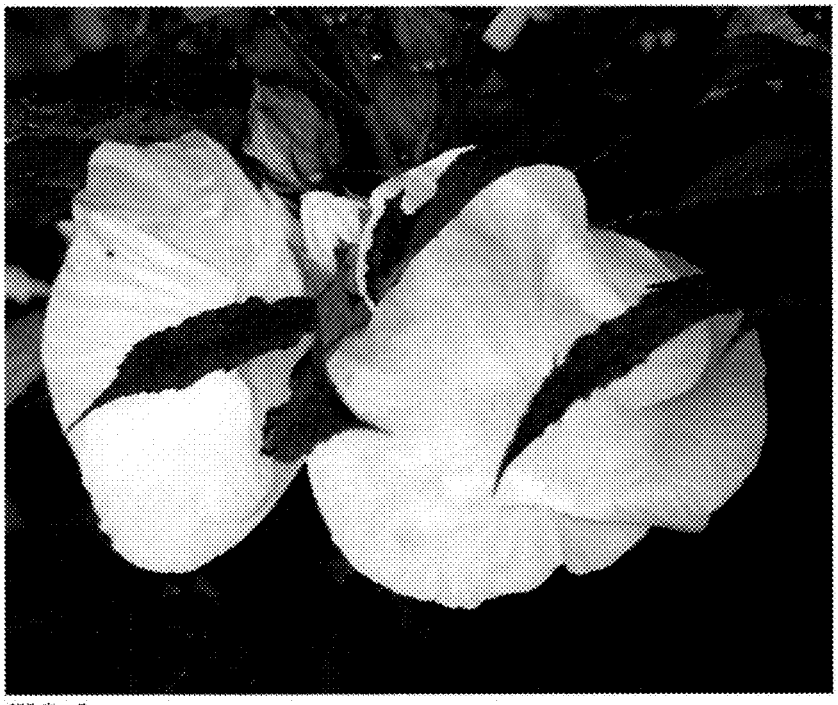
FIG. 2 shows a close-up of some flowers and a bud.
Figure 3:
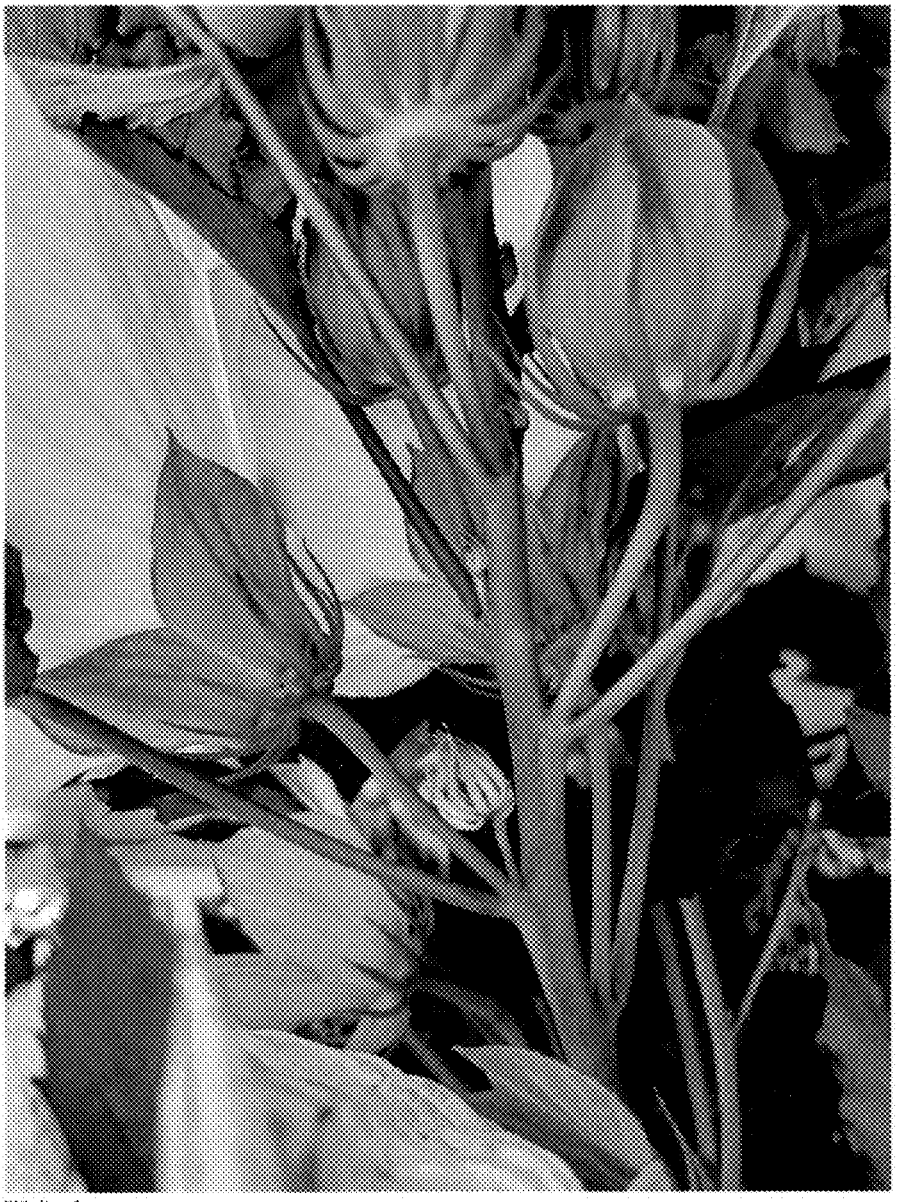
FIG. 3 shows the distal stem with a flower and developing bud on a single node.

The following descriptions and color references are based on the 2015 edition of The Royal Horticultural Society Colour Chart except where common dictionary terms are used. The new plant, *Hibiscus* 'Cookies and Cream', has not been observed in all possible environments. The phenotype may vary slightly with different environmental conditions, such as temperature, light, fertility, moisture, and maturity levels, but without any change in the genotype. The following observations and size descriptions are of a three-year-old plant in the loamy-sand, open-field full-sun display garden of a nursery in Zeeland, MI with supplemental fertilizer and water as needed. The plants are of natural habit and were not treated with plant growth regulators, nor were they pinched at any time in the growth year.

Parentage: The parent is the unreleased, non-patented, proprietary *Hibiscus* known by the breeder code 19-268-1;

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2 cm diameter, fleshy; root color creamy yellow nearest RHS 161D depending on soil type.

*Crop time*.—Under normal summer growing conditions 12 to 16 weeks to flower in a four-liter container from cutting without vernalization. Plant vigor is very good.

Plant description:

*Plant habit*.—Hardy herbaceous perennial with about 26 thick, upright, heavily branched stems producing a rounded mound to about 90 cm tall and about 126 cm wide; flowering in distal one-third of the plant.

*Stem*.—Cylindrical, glabrous, glaucous; to about 88 cm long and about 19 mm diameter at the base, average about 82 cm long and about 12 mm diameter at base; heavily branched.

*Stem color*.—Proximally nearest RHS 138C, distally variable nearest RHS 139B and between RHS N186C and RHS N186B.

*Branches*.—To 15 per stem, average about 10 per stem; cylindrical, glabrous, glaucous; to about 22 cm long and 8 mm diameter at base, smaller distally.

*Lateral branch color*.—Proximally nearest RHS 138C; distally variable nearest RHS 139B and between RHS N186C and RHS N186B in regions exposed to high light.

*Internode*.—About 21 nodes per stem below unbranched portion; average 38 nodes per stem; internode length about 2.4 cm of an unpinched plant.

*Internode color*.—Same as surrounding stem.

Foliage description: Tri-lobed to penta-lobed, with lobes deeply dissected to petiole or midrib or nearly to petiole or midrib; alternate; coarsely and irregularly dentate; apex and side lobes acute; base cordate to rounded; glabrous and matte both abaxial and adaxial;

*Leaf blade size*.—To about 16.6 cm long and about 17.5 cm across, average blade size 14 cm long and 13.5 cm wide; no fragrance detected.

*Foliage color*.—Young expanding leaves — adaxial between RHS N187A and RHS N186C, abaxial nearest RHS 137C with a variable blush of nearest RHS 187A; mature leaves — adaxial between RHS N187A and RHS 187A with an undertone of nearest RHS NN137A, abaxial nearest RHS 147B.

*Veins*.—Palmate; lustrous adaxial; costate and matte abaxial.

*Vein color*.—Adaxial proximally nearest RHS 187C and distally nearest RHS 187A; abaxial veins variable, proximal midrib between RHS 160C and RHS 146D, toward lobe centers primary veins nearest RHS 145C, distally with more light exposure nearest RHS 187C and a blend between RHS 182A and RHS 182B.

*Petioles*.—Mostly cylindrical, proximally slightly applanate on adaxial side; glabrous and slightly lustrous; to about 9.5 cm long and 5 mm across at base, average size about 7 cm long and 4 mm wide at base.

*Petiole color*.—Adaxial between RHS 178A and RHS 183B; abaxial variable, proximally nearest RHS 146C, distally between RHS 146C and RHS 183B.

Flower description: Complete; perfect; actinomorphic; rotate; solitary; mostly outward facing; moderately cupped; rotate; lasting up to two days on the plant; to about 26 flowers per center main stem, 6 flowers per branch, and 48 flowers on the whole stem;

Flowering season: Beginning in late July to early August and continuing for at least twelve weeks, with flowers repeating in succession in the distal unbranched portion producing multiple flowers at a single node;

Flower size: To about 15 cm across natural spread, 10 cm deep, and 18 cm across if flattened, decreasing in size slightly in size distally and later in the season;

*Buds one day prior to anthesis*.—Ellipsoidal with rounded apex and bluntly truncate base; sepals adpressed to petals; to about 5 cm long and about 3.5 cm diameter near middle.

*Bud color one day prior to anthesis*.—Exposed petal color main portion nearest RHS 11D, distal margin portion variably blushed nearest RHS 59D, and distal veins with light blush to nearly solid RHS 59C, and calyx adaxial basal portion nearest RHS 146D with veins nearest RHS 145C; abaxial nearest RHS 145A; purplish-red blush more strongly developed during cooler weather conditions and lacking in warmer weather conditions.

*Epicalyx*.—Average about 15 to 17 per flower; linear; entire, with margin micro-ciliolate; micro-puberulent, dull surfaces both abaxial and adaxial; sharply acute apex and truncate base; arcuate upwards near apex; to about 26 mm long and about 3.5 mm wide at base.

*Epicalyx color*.—Adaxial nearest RHS 146D and abaxial between RHS 137B and RHS 138A without anthocyanin blush.

*Calyx*.—Campanulate, form star-shaped hypanthium; to about 25 mm deep and 70 mm wide at apices.

*Sepals*.—Five; ovate; acute apex; margin entire, edentate; abaxial micro-puberulent and matte, adaxial glabrous and matte; about 37 mm long, about 24 mm wide at fusion, basal 16 mm fused.

*Sepal color*.—Adaxial basal portion nearest RHS 146D with veins nearest RHS 145C; abaxial nearest RHS 145A without anthocyanin blush.

*Inflorescence*.—Up to 48 per main stem and branches without pinching; producing multiple flowers per node in succession in the distal peduncle.

*Flower lastingness*.—Persist for one to two days; effective for at least 8 weeks beginning late July or early August.

*Flower fragrance*.—No detectable fragrance.

*Petals*.—Five; glabrous adaxial and abaxial; adaxial eye zone of about the proximal 15 mm lustrous, remaining distal adaxial portion and entire abaxial matte; adnate to the androecium to form a column, imbricate to about 90% overlapping at widest part (petals overlapping both petals on either side, so two petals about 10% not overlapping a third petal); margin undulation slight; with inside leading edge of petals frequently folded under an average of about 33 mm; palmately veined, primary veins slightly impressed on adaxial and slightly costate abaxial; surface slightly rippled along veins; apex rounded with distinct basal claw and limb; margins entire, edentate.

*Petal size*.—To about 13 cm across including folded portion and about 10 cm long, claw base about 8 mm across.

*Petal color*.—In warmer conditions adaxial basal and eye nearest RHS NN155A, distal portion nearest RHS NN155C, with proximal veins translucent to nearest RHS 156C and distal veins nearest NN155B; abaxial proximal 10 mm nearest RHS NN155A, distally nearest RHS NN155C; in cooler weather development distal adaxial and abaxial margin portion variably blushed nearest RHS 59D, and distal veins with light blush to nearly solid RHS 59C, typically the purplish-red blushing is stronger on abaxial than adaxial.

*Flower lastingness*.—One to two days.

*Gynoecium*.—Single; partially enclosed in column. Column: glabrous and lustrous; about 35 mm long and about 9 mm across at base; with pistil exserted about 10 mm; Column color: nearest RHS NN155C; Style: micro-puberulent in region exserted above column; about 50 mm long, penta-furcate in about distal 10 mm, branch diameter about 1 mm; color nearest RHS NN155B in exposed portion, and RHS NN155B portion enclosed in column; Stigma: typically, five; globose, flattened proximally, puberulent; about 2 mm in diameter and 1 mm tall; color in nearest RHS NN155A; Ovary: superior; cone with a slightly flatted top; longitudinally grooved in undulated pattern; rounded apex; and truncate base; about 11 mm across at base and about 8 mm tall; color nearest RHS 145C.

*Androecium*.—Attached to column. Filaments: numerous, about 100, attached starting about 11 mm from base to 2 mm from apex of column; to about 3 mm long, about 0.2 mm diameter; color between RHS NN155B and RHS N155C; Anthers: flattened reniform; dorsifixed; about 2 mm across, 2 mm long, and about 1 mm thick; color nearest RHS 11D; Pollen: abundant, globose, less than 0.1mm across; color nearest RHS 11C.

Pedicel: Cylindrical; glabrous; lustrous in distal portion beyond abscission point; length from base of sepal to abscission point about 17 mm long, from abscission point to stem node about 82 mm long; about 3.5 mm wide; longer on early flowers and decreasing in distal flowers;

Pedicel color: Nearest RHS 146D proximal abscission point, and nearest RHS 146B distal abscission point;

Peduncle: Cylindrical; glabrous; glaucous; flowering in upper 68 cm; to about 28 cm tall and about 12 mm diameter from below unbranched portion;

Peduncle color: Proximally nearest RHS 138C, distally variable nearest RHS 139B and between RHS N186C and RHS N186B;

Fruit: And seed: not yet observed;

Resistance: *Hibiscus* 'Cookies and Cream' has not displayed any pest and disease resistance beyond that typical of hardy perennial *Hibiscus*. The plant grows best with plenty of moisture. Hardiness at least from USDA zone 4 through 9.

I claim:

1. A new cultivar of hardy herbaceous perennial *Hibiscus* hybrid plant named 'Cookies and Cream' as herein illustrated and described.

* * * * *